(12) United States Patent
Yamagami et al.

(10) Patent No.: US 11,339,135 B2
(45) Date of Patent: May 24, 2022

(54) METHOD FOR PRODUCING TRIAZINE COMPOUND

(71) Applicant: MITSUBISHI TANABE PHARMA CORPORATION, Osaka (JP)

(72) Inventors: Takafumi Yamagami, Osaka (JP); Souta Yamasaki, Osaka (JP); Tomofumi Setsuta, Osaka (JP); Ryo Sakakibara, Osaka (JP); Yosuke Matsumura, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 463 days.

(21) Appl. No.: 16/464,562

(22) PCT Filed: Nov. 29, 2017

(86) PCT No.: PCT/JP2017/042769
§ 371 (c)(1),
(2) Date: May 28, 2019

(87) PCT Pub. No.: WO2018/101312
PCT Pub. Date: Jun. 7, 2018

(65) Prior Publication Data
US 2021/0380541 A1  Dec. 9, 2021

(30) Foreign Application Priority Data

Nov. 30, 2016  (JP) .............................. JP2016-232890

(51) Int. Cl.
*C07D 253/06* (2006.01)
*C07D 253/07* (2006.01)

(52) U.S. Cl.
CPC .................................. *C07D 253/07* (2013.01)

(58) Field of Classification Search
CPC .................................................... C07D 253/06
See application file for complete search history.

(56) References Cited

U.S. PATENT DOCUMENTS

| 4,513,135 A | 4/1985 | Wong et al. |
| 4,851,411 A | 7/1989 | Pitet et al. |
| 2017/0044115 A1 | 2/2017 | Ushirogochi et al. |

FOREIGN PATENT DOCUMENTS

| JP | 58-162582 A | 9/1983 |
| JP | 1-117875 A | 5/1989 |
| WO | WO 2010/001220 A1 | 1/2010 |

(Continued)

OTHER PUBLICATIONS

Desroy et al., "Novel HldE-K Inhibitors Leading Attenuated Gram Negative Bacterial Virulence", J. Med. Chem., 2013, vol. 56, 2013, pp. 1418-1430.

Fatutta, "2-Glyoxylylcoumarone and its Derivatives", Gazzetta Chimica Italiana, 1959, vol. 89, pp. 1598-1607, with English abstract.

Floyd et al., "The Oxidation of Acetophenones to Arylglyoxals with Aqueous Hydrobromic Acid in Dimethyl Sulfoxide" J. Org. Chem., vol. 50, No. 25., 1985, pp. 5022-5027.

He et al., "Synthesis of Some Heterocycles from α-Ketohemithioacetal", Chinese Journal of Organic Chemistry, vol. 21, 2001, No. 5, pp. 392-394, with English abstract.

(Continued)

*Primary Examiner* — Bruck Kifle
(74) *Attorney, Agent, or Firm* — Birch, Stewart, Kolasch & Birch, LLP

(57) ABSTRACT

The present invention provides an industrially advantageous method for producing a 3,5-disubstituted triazine compound that is useful as an active pharmaceutical ingredient. More specifically, the present invention provides a production method, whereby it becomes possible to efficiently produce a 3-oxo-5-substituted triazine in water without the need to isolate an intermediate that may have mutagenicity, and it also becomes possible to perform the production without the need to isolate a product in each of multiple steps. Namely, the present invention provides a method for producing a compound represented by formula I or a salt thereof, the method including a step of reacting a compound represented by the following formula IV or a salt thereof with a base in water, and optionally including a step of forming a salt thereof. Specifically, the present invention provides a method for producing a compound represented by formula I or a salt thereof, the method including a step of derivatizing a compound represented by formula II or a salt thereof into a corresponding compound represented by formula III, a salt thereof, or a derivative thereof, then a step of reacting the resulting compound, a salt thereof, or a derivative thereof with aminourea or a salt thereof in water to produce a compound represented by formula IV or a salt thereof, and then a step of reacting the resulting compound or a salt thereof in the presence of a base.

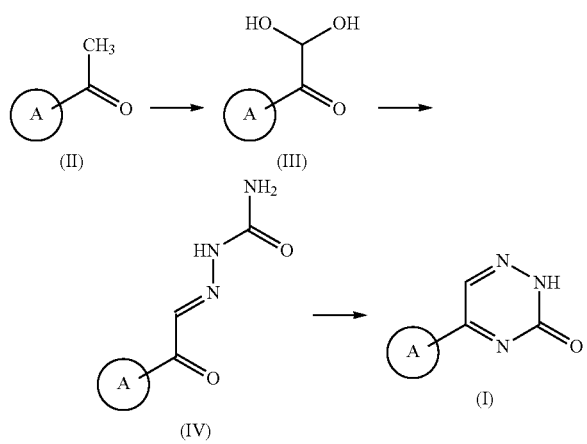

(wherein ring A represents an optionally substituted aryl group or an optionally substituted heteroaryl group)

15 Claims, No Drawings

(56) References Cited

FOREIGN PATENT DOCUMENTS

WO    WO 2015/163427 A1    10/2015

OTHER PUBLICATIONS

International Preliminary Report on Patentability and the Written Opinion of the International Searching Authority for International Application No. PCT/JP2017/042769, dated Jun. 4, 2019.
International Search Report for International Application No. PCT/JP2017/042769 dated Feb. 13, 2018.
Oleinik et al., "Synthesis and Antimicrobial Effect of Materials Obtained on the Basis of 5-Arylfuryl-2-Carbonyl Compounds", Khimiko-Farmatsevticheskii Zhurnal, vol. 8, No. 5, May 1974, pp. 7-13 (12 pages total).
Pathak et al., "Synthesis of Some New Fluorine Containing Oxazoles, Oxadiazoles, Thiadiazoles, and Triazines", J. Indian Chem. Soc., vol. 70, Jun. 1993, pp. 539-542.
Vinot et al., "Preparation and Properties of 5,6-disubstituted as-triazin-3-ones", Bulletin de la Societe Chimique de France, No. 12, 1972, pp. 4637-4642, with English abstract.
Yur'ev et al., "Chemistry of Selenophene. XIX. 2-Acetoselenophene in the Synthesis of α- and β-Ketoaldehydes of the Selenophene Series", Journal of General Chemistry of the USSR, vol. 29, No. 8, 1959, pp. 2561-2564.
European Search Report for Appl. No. 17875693.8 dated Jul. 2, 2020.
Giannella, M., et al, Su alcuni gliossali a nucleo isossazolico ed assazalico e loro derivati = [On some glyoxals with isoxazole and oxazole nuclei and their derivatives] Bollettino Chimico Farmaceutico, 1966, vol. 105, No. 10, pp. 708-718.

METHOD FOR PRODUCING TRIAZINE COMPOUND

TECHNICAL FIELD

The present invention relates to a method for efficiently producing a 3,5-disubstituted triazine compound. Especially, the present invention relates to an industrially advantageous production method which may produce 3-oxo-5-substituted triazine useful as an intermediate of medicines and the like with high purity.

BACKGROUND ART 3-oxo-5-substituted triazine is a compound useful as an intermediate of medicines and the like. For example, said compound may be used in synthesizing a 3,5-disubstituted triazine compound having an aldosterone synthase inhibitory activity (Patent Document 1) and the like.

3-oxo-5-substituted triazine, which is a key intermediate in the synthesis of a 3,5-disubstituted triazine compound, may be produced by cyclizing a corresponding imine (Nonpatent Document 1). Also, said imine derivative may be produced by converting an alkanoyl group in a corresponding starting material into a glyoxal group (Nonpatent Document 2), and reacting the resulting compound with aminourea (Nonpatent Document 3). However, in order to produce the imine derivative with high purity by these methods, it is essential to purify and dry the glyoxal derivative, then accurately add thereto 1 mol of aminourea relative to 1 mol of the isolated glyoxal derivative, and purify the resulting imine derivative. If the cyclizing reaction is carried out without purifying the imine derivative, a side reaction may proceed due to the residual aminourea or the like, and it is necessary to remove the by-product impurities by chromatography or the like after the cyclizing reaction (Patent Document 2 and Nonpatent Document 4). Namely, it is essential in the conventional art to purify the final product 3-oxo-5-substituted triazine by chromatography or the like, and carry out isolation procedures such as drying and purification of the various intermediates. Thus, the conventional art is not an appropriate method for industrially producing 3-oxo-5-substituted triazine with high purity from a corresponding starting material having an alkanoyl group. Also, in these methods which require the isolation procedures in each step, various intermediates having a glyoxal group, aminourea, and the like may have mutagenicity and/or sublimability. Accordingly, these methods also have a problem of worker safety in the large-scale production.

CITATION LIST

Patent Document

Patent Document 1: WO 2015/163427 pamphlet
Patent Document 2: WO 2010/001220 pamphlet

Nonpatent Document

Nonpatent Document 1: Chinese J. Org. Chem., 2001, 21, 392.
Nonpatent Document 2: J. Org. Chem., 1985, 50, 5022.
Nonpatent Document 3: J. Indian Chem. Soc., 1993, 70, 539.
Nonpatent Document 4: J. Med. Chem., 2013, 56, 1418.

SUMMARY OF THE INVENTION

Problems to be Solved by Invention

The present invention relates to a method for producing a 3,5-disubstituted triazine compound. Especially, the present invention provides an industrially advantageous production method which may produce a key intermediate 3-oxo-5-substituted triazine with high purity.

Means to Solve Problems

The present inventors have earnestly studied, as a result thereof found a method for producing a compound represented by formula I:

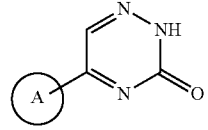

(I)

(wherein ring A represents an optionally substituted aryl group or an optionally substituted heteroaryl group) or a salt thereof with high purity and high efficiency, and completed the present invention. Namely, the present invention provides a method for producing a compound represented by formula I:

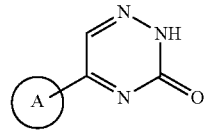

(I)

(wherein ring A represents an optionally substituted aryl group or an optionally substituted heteroaryl group) or a salt thereof, said method comprising a step of reacting a compound represented by formula IV:

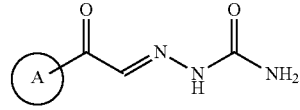

(IV)

(wherein ring A represents an optionally substituted aryl group or an optionally substituted heteroaryl group) or a salt thereof with a base in water, and optionally comprising a step of forming a salt thereof.

More specifically, the present invention provides a method for producing the compound represented by formula I or a salt thereof, said method comprising a step of reacting a compound represented by formula II:

(wherein ring A represents an optionally substituted aryl group or an optionally substituted heteroaryl group) or a salt thereof with a glyoxalization reagent to produce a compound represented by formula III:

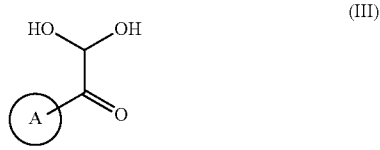

(wherein ring A represents an optionally substituted aryl group or an optionally substituted heteroaryl group), a salt thereof, or a derivative thereof, a step of reacting the resulting compound, a salt thereof, or a derivative thereof with aminourea or a salt thereof in water to produce a compound represented by formula IV:

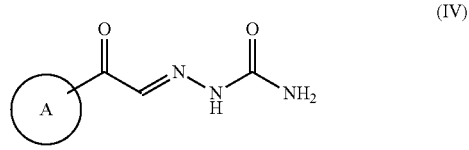

(wherein ring A represents an optionally substituted aryl group or an optionally substituted heteroaryl group) or a salt thereof, and a step of reacting the resulting compound or a salt thereof with a base in water to produce the compound represented by formula I or a salt thereof. According to the method of the present invention, the compound represented by formula I or a salt thereof may be efficiently produced. Also, after the reaction of the final step is completed, the compound represented by formula I or a salt thereof may be produced with high purity just by collecting the resulting precipitates by filtration from the reaction mixture.

Effect of Invention

According to the present invention, 3-oxo-5-substituted triazine useful as an intermediate of medicines and the like may be produced by an industrially appropriate method. More specifically, 3-oxo-5-substituted triazine may be produced with high purity and high efficiency by derivatizing the compound represented by formula II or a salt thereof into the compound represented by formula III, a salt thereof, or a derivative thereof, reacting the resulting compound, a salt thereof, or a derivative thereof with aminourea in water to highly efficiently derivatize it into the imine derivative represented by formula IV or a salt thereof, and subsequently cyclizing the resulting imine derivative or a salt thereof in water under a basic condition. These reactions may be carried out by using water as a solvent, and thus are industrially advantageous in both of safety and cost. Also, the method of the present invention has high safety even in the point that it is not necessary to isolate an intermediate which may have mutagenicity and/or sublimability. Further, the method of the present invention is industrially advantageous also in that the purity of the target 3-oxo-5-substituted triazine may be easily improved by optionally collecting the imine derivative or a salt thereof by filtration and then using it in the next step, and thus isolation procedures which need time and effort such as purification and drying are not required at all throughout the whole steps even in that case.

MODE FOR CARRYING OUT THE INVENTION

The definition of each group in the present description may be freely combined with each other unless otherwise specified.

Examples of the term of "halogen atom" in the present description include a fluorine atom, a chlorine atom, a bromine atom, and an iodine atom, preferable examples thereof include a fluorine atom and a chlorine atom, and especially preferable examples thereof include a chlorine atom.

Examples of the term of "alkyl group" in the present description include straight or branched alkyl groups having 1 to 6 carbon atoms ($C_{1-6}$). Specific examples thereof include a methyl group, an ethyl group, an n-propyl group, an i-propyl group, an n-butyl group, and a t-butyl group. Especially preferable examples thereof include a methyl group.

Examples of the term of "alkoxy group" in the present description include straight and branched alkoxy groups having 1 to 6 carbon atoms ($C_{1-6}$). Specific examples thereof include a methoxy group, an ethoxy group, an n-propoxy group, and a t-butoxy group. Especially preferable examples thereof include a methoxy group.

Examples of the term of "cycloalkyl group" in the present description include monocyclic saturated hydrocarbon groups having 3 to 8 carbon atoms ($C_3$-8) and an adamantyl group. The term of "cycloalkyl group" also includes a group wherein two ring carbon atoms are cross-linked by an alkylene group to form a bicyclo ring. Specific examples of "cycloalkyl group" include a cyclopropyl group, a cyclobutyl group, a cyclopentyl group, a cyclohexyl group, a cycloheptyl group, a bicyclo[2.2.2]octyl group, and an adamantyl group.

Examples of the term of "aryl group" in the present description include 6 to 10 membered aromatic carbocyclic group. Specific examples thereof include monocyclic or bicyclic aryl groups such as a phenyl group and a naphthyl group. Especially preferable examples thereof include a phenyl group.

Examples of the term of "heteroaryl group" in the present description include 5 to 10 membered aromatic heterocyclic groups comprising 1 to 4 heteroatom(s) independently selected from the group consisting of a sulfur atom, an oxygen atom, and a nitrogen atom, and preferable examples thereof include monocyclic or bicyclic heteroaryl groups. More preferable examples thereof include 5 to 10 membered monocyclic or bicyclic heteroaryl groups comprising 1 to 2 heteroatom(s) independently selected from the group consisting of a sulfur atom, an oxygen atom, and a nitrogen atom. Also, other preferable examples thereof include 5 to 10 membered monocyclic or bicyclic heteroaryl groups comprising at least one nitrogen atom and further optionally comprising one heteroatom selected from the group consisting of a sulfur atom, an oxygen atom, and a nitrogen atom.

Specific examples thereof include a pyrrolyl group, a furanyl group, a thienyl group, an imidazolyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an indazolyl group, a benzimidazolyl group, a benzothiazolyl group, a benzofuranyl group, a quinolyl group, an isoquinolyl group, an imidazopyridyl group, and a benzopyranyl group.

Examples of the "partially hydrogenated heteroaryl group" among the "optionally partially hydrogenated heteroaryl group" in the present description include a group formed by partially hydrogenating the above heteroaryl group, and also include a cyclic group wherein a phenyl group is fused to an aliphatic heterocyclic group. Specific examples thereof include an imidazolinyl group, a dihydrobenzofuranyl group, a dihydrobenzopyranyl group, a tetrahydroimidazopyridyl group, and an isoindolinyl group.

Examples of the "optionally partially hydrogenated heteroaryl group" include a pyrrolyl group, a furanyl group, a thienyl group, an imidazolyl group, an imidazolinyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, and a dihydrobenzopyranyl group, and preferable examples thereof include a thienyl group, a pyridyl group, an indolyl group, an indazolyl group, an isoquinolyl group, a dihydrobenzofuranyl group, a dihydrobenzopyranyl group, and a benzothiazolyl group.

Examples of the term of "aliphatic heterocyclic group" in the present description include 4 to 9 membered cyclic groups comprising 1 to 3 heteroatom(s) independently selected from the group consisting of a sulfur atom, an oxygen atom, and a nitrogen atom. Examples of the "aliphatic heterocyclic group" also include a group wherein two ring carbon atoms are cross-linked by an alkylene group to form a bicyclo ring. Specific and preferable examples thereof include an azetidinyl group, an oxetanyl group, a pyrrolidinyl group, a tetrahydrothiophenyl group, a tetrahydrofuranyl group, a piperidinyl group, a homopiperidinyl group, a piperazinyl group, a morpholinyl group, a thiomorpholinyl group, a homomorpholinyl group, a tetrahydrothiopyranyl group, a tetrahydropyranyl group, an azabicyclo[2.2.2]octyl group (quinuclidinyl group), an azabicyclo[3.2.1]octyl group, an oxabicyclo[3.3.1]nonyl group, a diazabicyclo[2.2.1]heptyl group, and an oxo-9-azabicyclo[3.3.1]nonyl group.

Also, other preferable examples of the "aliphatic heterocyclic group" include 4 to 9 membered aliphatic heterocyclic groups comprising at least one nitrogen atom, and further optionally comprising one heteroatom selected from the group consisting of a sulfur atom, an oxygen atom, and a nitrogen atom. Specific examples thereof include an azetidinyl group, a pyrrolidinyl group, a piperidinyl group, a piperazinyl group, a morpholinyl group, a thiomorpholinyl group, a homomorpholinyl group, an azabicyclo[2.2.2]octyl group (quinuclidinyl group), an azabicyclo[3.2.1]octyl group, and a diazabicyclo[2.2.1]heptyl group.

Further, still other preferable examples of the "aliphatic heterocyclic group" include 4 to 9 membered aliphatic heterocyclic groups comprising 1 to 2 heteroatom(s) selected from an oxygen atom and a nitrogen atom. Specific examples thereof include an oxetanyl group, a tetrahydrofuranyl group, a tetrahydropyranyl group, a pyrrolidinyl group, a piperidinyl group, and a homopiperidinyl group.

The term of "isolation (or isolate, isolating, or isolated)" in the present description refers to carrying out a procedure such as purification by recrystallization, chromatography, or the like, and drying a resulting product. The term of "collection (or collect, collecting, or collected) by filtration" is not included in "isolation (or isolate, isolating, or isolated)" in the present description.

The term of "collection (or collect, collecting, or collected) by filtration" in the present description refers to separating a solid component from a reaction mixture by a procedure such as filtration and centrifugation. In the procedure, the solid component collected by filtration may be washed with water.

In the present description, the compound of formula I has tautomeric properties, and includes both of the following structures.

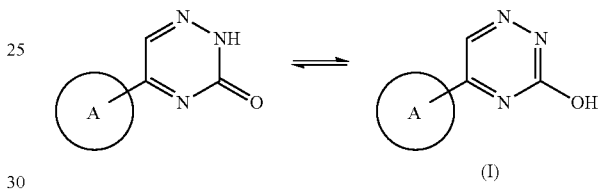

(I)

Thus, "carbonyl group of the compound represented by formula I" in the present description refers to the same substituent as "hydroxyl group of the compound represented by formula I".

Also, in the present description, the compound of formula IV has tautomeric properties, and includes both of the following structures.

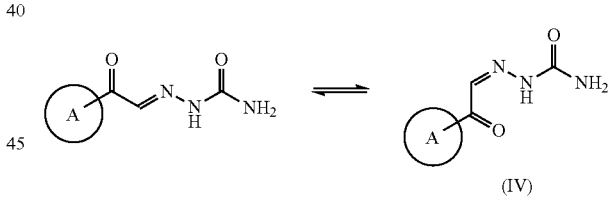

(IV)

Further, the compound represented by formula III is in equilibrium with a compound represented by formula III':

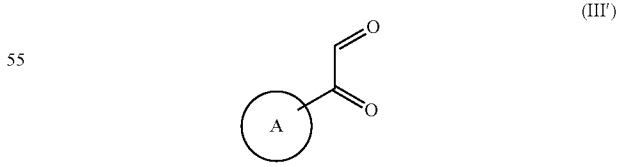

(III')

(wherein ring A represents an optionally substituted aryl group or an optionally substituted heteroaryl group) in the presence of water, and thus, examples of the derivative of the compound represented by formula III in the present description include the compound represented by formula III'.

The present invention relates to the following production methods (1) to (6).

(1) In one embodiment, the present invention includes a method for producing a compound represented by formula I:

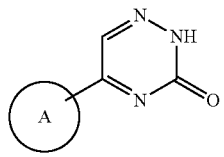
(I)

(wherein ring A represents an optionally substituted aryl group or an optionally substituted heteroaryl group) or a salt thereof, said method comprising a step of reacting a compound represented by formula IV:

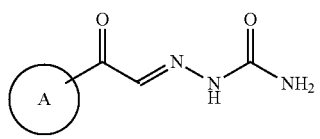
(IV)

(wherein ring A represents an optionally substituted aryl group or an optionally substituted heteroaryl group) or a salt thereof with a base in water, and optionally comprising a step of forming a salt thereof.

Examples of the base to be used include alkali metal hydroxides such as sodium hydroxide and potassium hydroxide, and alkaline earth metal hydroxides such as calcium hydroxide. Preferable examples thereof include alkali metal hydroxides such as sodium hydroxide and potassium hydroxide, and especially preferable examples thereof include sodium hydroxide.

Preferable examples of the amount of the base to be used include 1 to 2 mol(s) relative to 1 mol of the compound represented by formula IV or a salt thereof.

The reaction may preferably proceed at 40° C. to 100° C., and especially preferably proceed at 50° C. to 70° C.

After the reaction is completed, the reaction solution is optionally subjected to a procedure such as neutralization, and the compound of formula I or a salt thereof may be produced with high purity just by collecting the resulting precipitates from the reaction mixture by filtration. Optionally, the compound of formula I or a salt thereof may be produced with higher purity by washing the reaction solution with an organic solvent before the above procedure such as neutralization.

(2) In another embodiment, the present invention includes the method according to (1), said method comprising a step of reacting a compound represented by formula III:

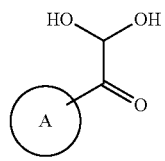
(III)

(wherein ring A represents an optionally substituted aryl group or an optionally substituted heteroaryl group), a salt thereof, or a derivative thereof with aminourea or a salt thereof in water to produce the compound represented by formula IV or a salt thereof, and then a step of subjecting the resulting compound or a salt thereof to the step(s) according to (1).

The present reaction may preferably proceed under an acidic condition. Preferable examples of the acid to be used include inorganic acids such as hydrochloric acid, hydrobromic acid, phosphoric acid, and sulfuric acid, and organic acids such as acetic acid, trifluoroacetic acid, citric acid, and maleic acid, and especially preferable examples thereof include hydrochloric acid and hydrobromic acid. Preferable examples of the amount of the acid to be used include 0.1 to 1.0 mol(s) relative to 1 mol of the compound represented by formula III, a salt thereof, or a derivative thereof.

Preferable examples of the amount of the aminourea or a salt thereof to be used include 0.95 to 1.2 mol(s) relative to 1 mol of the compound represented by formula III, a salt thereof, or a derivative thereof. Normally, in a conversion reaction of a glyoxal to an imine derivative such as a conversion reaction to the compound of formula IV or a salt thereof, an excess amount of aminourea in a reaction system causes the resulting imine derivative such as the compound of formula IV or a salt thereof to further react with aminourea or a salt thereof to produce a by-product, and thus the amount of aminourea or a salt thereof to be used needs to be rigorously controlled. On the contrary, the present reaction is carried out in water, and the water-insoluble compound of formula IV or a salt thereof precipitates as soon as it is produced and does not have a risk of a side reaction with the water-soluble aminourea or a salt thereof. Thus, the amount of aminourea or a salt thereof to be used does not need to be rigorously controlled in the present reaction.

Aminourea may be used in the form of a salt. It is preferable to use a salt of aminourea, because a salt would make the handling of aminourea having mutagenicity easy, and an acid which forms a salt with aminourea would promote the proceeding of the present reaction. Preferable examples of the salt of aminourea include hydrochloride and hydrobromide, and especially preferable examples include hydrochloride.

The reaction may preferably proceed at 30° C. to 100° C., and especially preferable proceed at 50° C. to 70° C.

It is preferable to use the resulting compound represented by formula IV or a salt thereof in the next step after collecting it by filtration, because the compound represented by formula I or a salt thereof may be produced with higher purity by such procedure. Especially, when an excess amount of aminourea or a salt thereof is used, it is preferable to collect the product by filtration after the present step is completed, and subject it to the next step. Namely, because the compound of formula IV or a salt thereof is water-insoluble, the water-soluble impurities, especially the residual aminourea may be removed just by washing with water after collecting it by filtration. As a result, the reaction in the next step may highly efficiently proceed, and it would become unnecessary to carry out a purification procedure for removing water-soluble impurities after the reaction of the next step is completed. Even when the compound of formula IV or a salt thereof is collected by filtration, it is not necessary to carry out an isolation procedure such as purification and drying in the present step.

Also, the compound represented by formula IV or a salt thereof may be subjected to the step(s) according to (1) without isolation of the compound or a salt thereof, or subjected to the step(s) according to (1) after isolation of the compound or a salt thereof. In a preferable embodiment, the compound represented by formula IV or a salt thereof is subjected to the step(s) according to (1) without isolation.

(3) In another embodiment, the present invention includes the method according to (2), said method comprising a step of reacting a compound represented by formula II:

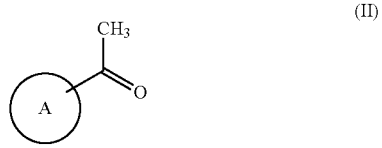

(wherein ring A represents an optionally substituted aryl group or an optionally substituted heteroaryl group) or a salt thereof with a glyoxalization reagent to produce the compound represented by formula III, a salt thereof, or a derivative thereof, and then a step of subjecting the resulting compound, a salt thereof, or a derivative thereof to the step(s) according to (2).

The derivatization of the compound represented by formula II or a salt thereof into the compound represented by formula III, a salt thereof, or a derivative thereof may be carried out in the presence of a glyoxalization reagent in an appropriate solvent or in the absence of solvent according to a method such as the method disclosed in Patent Document 2 or Nonpatent Document 2.

The present reaction may be preferably carried out in the absence of solvent. When a solvent is used in the present reaction, any solvent may be used as long as it does not disturb the present reaction, and preferable examples thereof include aromatic hydrocarbons such as toluene, aliphatic hydrocarbons such as heptane, halogenated aliphatic hydrocarbons such as methylene chloride, nitriles such as acetonitrile, sulfoxides such as dimethylsulfoxide, ethers such as tetrahydrofuran, water, and mixtures thereof. Alternatively, a sulfoxide, water, or the like used as a reagent may be used at an excess amount as a solvent. When a solvent is used, the preferable amount of the solvent may be 5 to 10 times by volume ratio relative to the weight of the compound represented by formula II or a salt thereof.

Examples of the glyoxalization reagent to be used include a mixed solution of hydrobromic acid and a sulfoxide, and selenium oxide, and preferable examples thereof include a mixed solution of hydrobromic acid and dimethylsulfoxide. Preferable examples of the amount of the glyoxalization reagent to be used include 3 to 5 mols relative to 1 mol of the compound represented by formula II or a salt thereof.

The reaction may preferably proceed at 40° C. to 100° C., and especially preferably proceed at 50° C. to 70° C. The temperature of 60° C. may be especially preferable in order to promote the reaction and inhibit the degradation of the product.

When a by-product accumulates in the reaction system and disturbs the proceeding of the reaction, it is preferable to remove the by-product from the reaction system. For example, when a by-product compound which exists in gas at the reaction temperature such as dimethyl sulfide is produced, the conversion ratio and reaction yield may be improved by replacing the gas in the reaction container with an inert gas which does not affect the reaction.

If the resulting compound of formula III, a salt thereof, or a derivative thereof is collected by filtration and then used in the next step, the compound of formula I or a salt thereof may be produced with higher purity. Even in this case, it is not necessary to carry out an isolation procedure such as purification and drying.

Further, the compound represented by formula III, a salt thereof, or a derivative thereof may be subjected to the step(s) according to (2) without isolation of the compound, a salt thereof, or a derivative thereof, or subjected to the step(s) according to (2) after isolation of the compound, a salt thereof, or a derivative thereof. In a preferable embodiment, the compound represented by formula III, a salt thereof, or a derivative thereof may be subjected to the step(s) according to (2) without isolation.

(4) In another embodiment, the present invention includes the method according to (2) or (3), said method comprising a step of collecting the compound represented by formula IV or a salt thereof by filtration. In another embodiment, the present invention includes the method according to (3), said method comprising a step of collecting the compound represented by formula III, a salt thereof, or a derivative thereof by filtration. In still another embodiment, the present invention includes the method according to any one of (1) to (3), said method comprising a step of reacting the compound represented by formula II or a salt thereof with a glyoxalization reagent to produce the compound represented by formula III, a salt thereof, or a derivative thereof, then a step of reacting the resulting compound, a salt thereof, or a derivative thereof with aminourea or a salt thereof in water without isolation of the compound, a salt thereof, or a derivative thereof to produce the compound represented by formula IV or a salt thereof, then a step of reacting the resulting compound or a salt thereof with a base in water without isolation of the compound or a salt thereof, and optionally a step of forming a salt thereof to produce the compound represented by formula I or a salt thereof. Even in these cases, it is not necessary at all to dry the intermediates collected by filtration, because all steps of the present invention are carried out in the absence of solvent or in a common solvent, water.

(5) In another embodiment, the present invention includes the method according to any one of (1) to (4), wherein ring A is an optionally substituted monocyclic or bicyclic aryl group. Especially, ring A is preferably a monocyclic or bicyclic aryl group optionally substituted with 1 to 3 group(s) independently selected from the group consisting of a halogen atom, an alkyl group, and an alkoxy group.

(6) In another embodiment, the present invention includes a method for producing a compound represented by formula V:

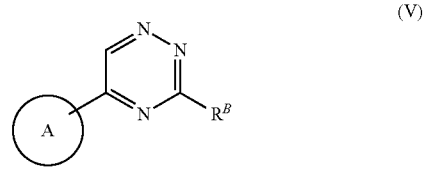

(wherein ring A represents an optionally substituted aryl group or an optionally substituted heteroaryl group and $R^B$ represents an optionally substituted aliphatic heterocyclic group) or a pharmaceutically acceptable salt thereof, said method comprising a step of producing the compound represented by formula I or a salt thereof by the method according to any one of (1) to (5), and then a step of producing the compound represented by formula V or a pharmaceutically acceptable salt thereof by any one of known methods, combined methods thereof, or the like.

In a preferable embodiment of said method, the compound V or a pharmaceutically acceptable salt thereof wherein
ring A is an optionally substituted monocyclic or bicyclic aryl group; and
$R^B$ is a group represented by formula VI:

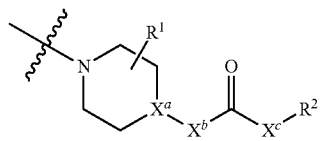

(VI)

(wherein $X^a$ represents $CR^{3a}$ or N;
(i) when $X^a$ represents $CR^{3a}$, then
$X^b$ represents $CHR^{3b}$ and $X^c$ represents O or $NR^{4c}$,
$X^b$ represents O and $X^c$ represents $NR^{4c}$, or
$X^b$ represents $NR^{4b}$ and $X^c$ represents O, $NR^{4c}$, or $CHR^{3c}$;
(ii) when $X^a$ represents N, then
$X^b$ represents $CHR^{3b}$ or C(=O) and $X^c$ represents $NR^{4c}$, or
$X^b$ represents $NR^{4b}$ and $X^c$ represents $CHR^{3c}$;
$R^{3a}$ represents a hydrogen atom, a hydroxy group, an alkyl group, or an amino group;
$R^{3b}$ and $R^{3c}$ represent each a group independently selected from the group consisting of a hydrogen atom, a hydroxy group, and an alkyl group;
$R^{4b}$ and $R^{4c}$ represent each a group independently selected from the group consisting of a hydrogen atom, an alkyl group, and a cycloalkyl group;
$R^1$ represents a hydrogen atom or an alkyl group;
$R^2$ represents
(i) an optionally substituted alkyl group,
(ii) an optionally substituted cycloalkyl group,
(iii) an optionally substituted aliphatic heterocyclic group,
(iv) an optionally partially hydrogenated and optionally substituted heteroaryl group, or
(v) a hydrogen atom, or
when $X^c$ represents $NR^{4c}$, $R^2$ and $R^{4c}$ are combined with each other at their terminals together with the nitrogen atom to which they are attached to form an aliphatic heterocyclic group optionally substituted with an optionally substituted alkyl group; and
the wavy line represents the point of attachment to the rest of molecule) is produced.

Preferable examples of ring A include a monocyclic or bicyclic aryl group optionally substituted with 1 to 3 group (s) independently selected from the group consisting of a halogen atom, an alkyl group, and an alkoxy group, and especially preferable examples thereof include a phenyl group or a naphthyl group optionally substituted with 1 to 3 group(s) independently selected from the group consisting of a halogen atom, an alkyl group, and an alkoxy group.

$R^B$ is preferably a group represented by formula VI, and a group wherein
$X^a$ represents N;
$X^b$ represents $CHR^{3b}$ or C(=O);
$X^c$ represents $NR^{4c}$;
$R^{3b}$ represents a group independently selected from the group consisting of a hydrogen atom, a hydroxy group, and an alkyl group;
$R^{4c}$ represents a group independently selected from the group consisting of a hydrogen atom, an alkyl group, and a cycloalkyl group;
$R^1$ represents a hydrogen atom or an alkyl group;
$R^2$ represents
(i) an optionally substituted alkyl group,
(ii) an optionally substituted cycloalkyl group,
(iii) an optionally substituted aliphatic heterocyclic group,
(iv) an optionally partially hydrogenated and optionally substituted heteroaryl group, or
(v) a hydrogen atom, or
$R^2$ and $R^{4c}$ are combined with each other at their terminals together with the nitrogen atom to which they are attached to form an aliphatic heterocyclic group optionally substituted with an optionally substituted alkyl group is preferable.

The conversion method of the compound represented by formula I or a salt thereof into the compound represented by formula V or a pharmaceutically acceptable salt thereof may be carried out according to any one of methods known to a skilled person or combined methods thereof such as the methods disclosed in the above Patent Document 1 or Patent Document 2. For example, the hydroxyl group (or carbonyl group) of the compound represented by formula I or a salt thereof may be converted into an appropriate leaving group such as a halogen atom or an alkoxy group by a known method, and then reacted with a compound represented by $R^B$—H (wherein $R^B$ represents an optionally substituted aliphatic heterocyclic group) or a derivative thereof to be converted into the compound represented by formula V or a pharmaceutically acceptable salt thereof.

Examples of such method include a method wherein the carbonyl group (or hydroxyl group) of the compound represented by formula I or a salt thereof is converted into a leaving group by a known method, then reacted with a compound represented by formula VII:

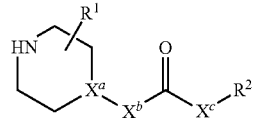

(VII)

(wherein $X^a$ represents $CR^{3a}$ or N;
(i) when $X^a$ represents $CR^{3a}$, then
$X^b$ represents $CHR^{3b}$ and $X^c$ represents O or $NR^{4c}$,
$X^b$ represents O and $X^c$ represents $NR^{4c}$, or
$X^b$ represents $NR^{4b}$ and XV represents O, $NR^{4c}$, or $CHR^{3c}$;
(ii) when $X^a$ represents N, then
$X^b$ represents $CHR^{3b}$ or C(=O) and $X^c$ represents $NR^{4c}$, or
$X^b$ represents $NR^{4b}$ and $X^c$ represents $CHR^{3c}$;
$R^{3a}$ represents a hydrogen atom, a hydroxy group, an alkyl group, or an amino group;
$R^{3b}$ and $R^{3c}$ represent each a group independently selected from the group consisting of a hydrogen atom, a hydroxy group, and an alkyl group;
$R^{4b}$ and $R^{4c}$ represent each a group independently selected from the group consisting of a hydrogen atom, an alkyl group, and a cycloalkyl group;
$R^1$ represents a hydrogen atom or an alkyl group;
$R^2$ represents
(i) an optionally substituted alkyl group,
(ii) an optionally substituted cycloalkyl group,
(iii) an optionally substituted aliphatic heterocyclic group,
(iv) an optionally partially hydrogenated and optionally substituted heteroaryl group, or (v) a hydrogen atom, or when $X^c$ represents $NR^{4c}$, $R^2$ and $R^{4c}$ are combined with each other at their terminals together with the nitrogen atom to which they are attached to form an aliphatic heterocyclic group optionally substituted with an optionally substituted alkyl group) or a salt thereof, and the functional group of the resulting compound or a salt thereof is optionally protected, deprotected, or the like to produce the compound represented by formula V or a pharmaceutically acceptable salt thereof. General descriptions of protecting groups and use thereof are described in T. W. Greene et al., "Protective Groups in Organic Synthesis", John Wiley & Sons, New York, 2006.

All compounds produced in each step of the present invention may also be produced in the form of a salt. The salt may be any one which may be usually industrially used, and examples thereof include inorganic acid salts such as hydrochloride, sulfate, phosphate, and hydrobromide, organic acid salts such as acetate, fumarate, oxalate, citrate, methanesulfonate, benzene sulfonate, tosylate, and maleate, and alkali metal salts such as sodium salt and potassium salt. The conversion of a compound into such a salt may be carried out according to a conventional method.

The term of "pharmaceutically acceptable salt" in the present description refers to any one of inorganic acid salts such as hydrochloride, sulfate, phosphate, and hydrobromide, and organic acid salts such as acetate, fumarate, oxalate, citrate, methanesulfonate, benzene sulfonate, tosylate, and maleate, and the like.

EXAMPLES

Hereinafter, the present invention is specifically illustrated by means of Examples and the like, but the present invention is not limited to them.

Each data of MS described in examples was measured by the following conditions.

(1) HPLC/LRMS

Device: Waters ZQ2000

Operation conditions: [Column] CAPCELLPACK C18 MGIII 5μ 4.6×50 mm, [Solvent] A: 10 mM $(NH4)_2CO_3$ in water, B: $CH_3CN$, [Gradient] A:B=90:10→0:100, 5 min, [Flow rate] 2 mL/min Measurement range: 0 to 8 min

Example 1

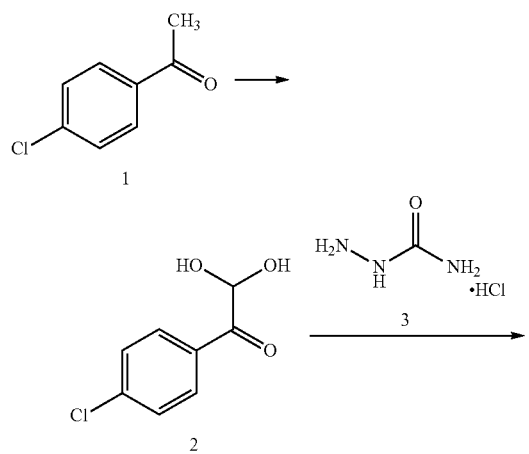

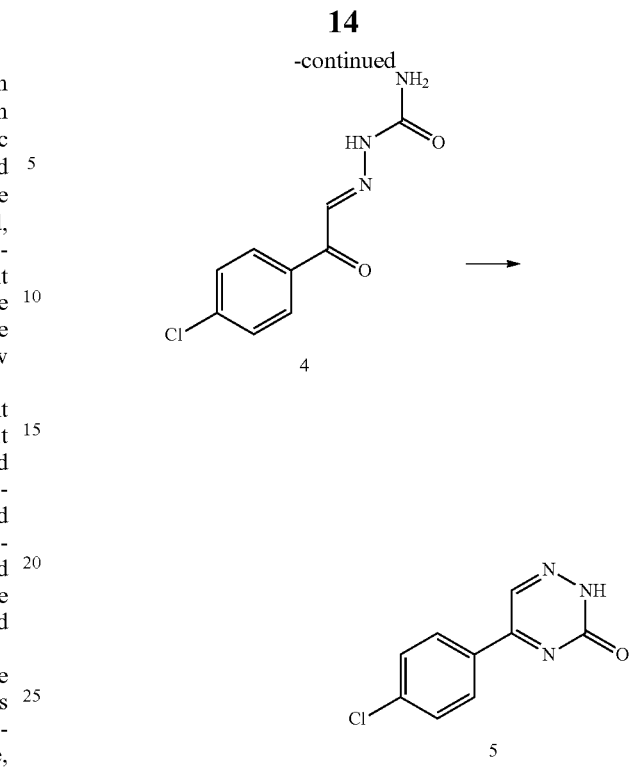

(1) To a solution of Compound 1 (4.61 g) in dimethylsulfoxide (32.3 mL) was added hydrobromic acid (47% aqueous solution, 13.8 mL) at room temperature. Dimethylsulfoxide (13.8 mL) was further added thereto, the resulting mixture was stirred at 60 to 70° C. overnight and then cooled to room temperature, water was added thereto, and the resulting Compound 2 was collected by filtration and washed with water.

(2) The wet body of Compound 2 obtained in the above (1) was directly suspended in water without drying it, an aqueous solution of aminourea hydrochloride (Compound 3, 1.51 g) was added thereto at 55 to 65° C., the resulting mixture was stirred overnight, and then the resulting Compound 4 was collected by filtration at the same temperature and washed with water.

(3) The wet body of Compound 4 obtained in the above (2) was directly suspended in water without drying it, an 8 mol/L aqueous solution of sodium hydroxide (4.27 mL) was added thereto at room temperature, and the resulting mixture was stirred at 60 to 62° C. for 1 hour. Water was further added thereto, and the resulting mixture was stirred at the same temperature overnight. Water was further added thereto, and the resulting mixture was stirred at the same temperature for 6 hours. After the reaction was completed, toluene and water were added to the reaction system, the resulting insoluble matters were filtered at room temperature, and then the resulting organic layer was separated. To the resulting aqueous layer was added acetic acid (8 mL) at the same temperature, and the resulting mixture was stirred at room temperature overnight. The resulting precipitates were collected by filtration, and dried to give Compound 5 (1.12 g) as a pale yellowish-white powder (40% yield based on Compound 3). ($^1$H NMR (DMSO-$d_6$): δ7.68 (d, J=8.5 Hz, 2H), 8.24 (d, J=8.5 Hz, 2H), 8.75 (s, 1H), 13.4 (s, 1H), LRMS (ESI) m/z: Calcd for $C_{10}H_9N_3O$ $[M+H]^+$ 208/210 Found: 207.9/209.9).

Example 2

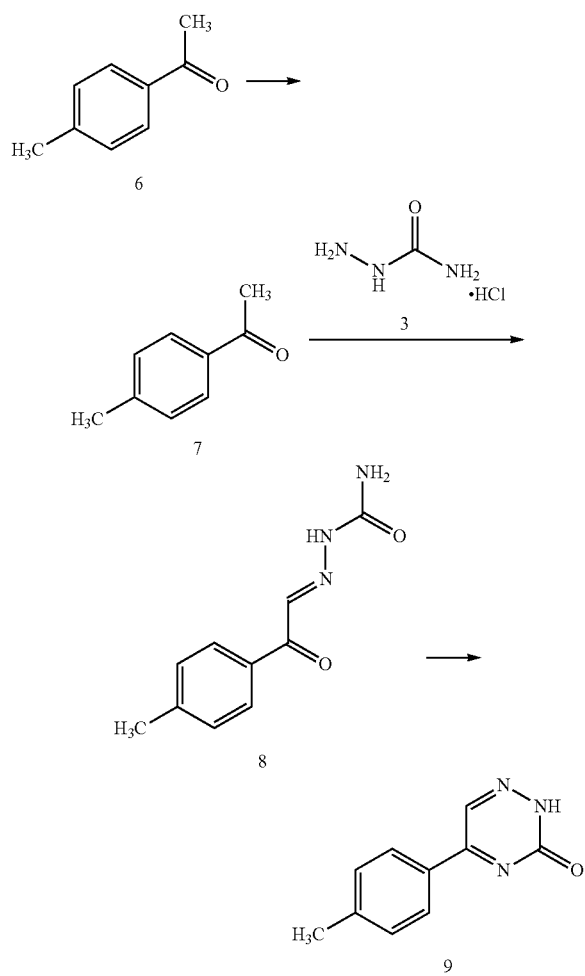

(1) To a solution of Compound 6 (100.77 g) in dimethylsulfoxide (700 mL) was added hydrobromic acid (48% aqueous solution, 300 mL) at room temperature, the resulting mixture was stirred at 60° C. for 4 hours and 40 minutes and then cooled to room temperature, water was added thereto, and the resulting precipitates were collected by filtration to give Compound 7 as a wet body.

(2) The wet body of Compound 7 obtained in the above (1) was directly suspended in water without drying it, an aqueous solution of aminourea hydrochloride (Compound 3, 149.73 g) was added thereto, the resulting mixture was stirred at 59 to 60° C. for 1 hour, and then the resulting Compound 8 was collected by filtration at the same temperature and washed with water.

(3) The wet body of Compound 8 obtained in the above (2) was directly suspended in water without drying it, an 8 mol/L aqueous solution of sodium hydroxide (164.89 mL) was added thereto at 55 to 60° C., and the resulting mixture was stirred at 59 to 60° C. for 2 hours and 40 minutes. After the reaction was completed, toluene was added to the reaction system, and the resulting organic layer was separated. To the resulting aqueous layer was added acetic acid (100 mL) at the same temperature and the resulting mixture was stirred at room temperature. The resulting precipitates were collected by filtration and dried to give Compound 9 (92.81 g) as a pale yellowish-white powder (75% yield based on Compound 3). ($^1$H NMR (DMSO-$d_6$): δ 2.31 (s, 3H), 7.40 (d, J=8.5 Hz, 2H), 8.13 (d, J=8.5 Hz, 2H), 8.70 (s, 1H), 13.3 (bs, 1H), LRMS (ESI) m/z: Calcd for $C_{10}H_9N_3O$ [M+H]$^+$188 Found: 187.9).

Examples 3 to 5

Each corresponding starting compound was treated in a similar manner to the above Example 1 to give each compound described in the following Table 1.

TABLE 1

| Ex. | Compound | MS | Yield [%] |
|---|---|---|---|
| 3 | ![structure] 2-methylphenyl triazinone | 188 [M + H]$^+$ | 59 |
| 4 | ![structure] naphthyl triazinone | 224 [M + H]$^+$ | 20 |
| 5 | ![structure] 4-methoxyphenyl triazinone | 204 [M + H]$^+$ | 86 |

INDUSTRIAL APPLICABILITY

The production method of the present invention is useful as a method for producing a 3,5-disubstituted triazine compound useful as an intermediate of active pharmaceutical ingredients or a synthetic intermediate thereof.

The invention claimed is:

1. A method for producing a compound represented by formula I:

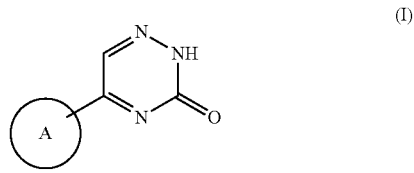

(I)

or a salt thereof, said method comprising a step of reacting a compound represented by formula IV:

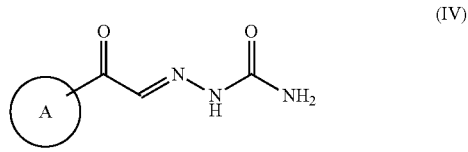

(IV)

or a salt thereof with a base in water, and optionally comprising a step of forming a salt thereof;
wherein ring A represents an optionally substituted aryl group or an optionally substituted heteroaryl group.

2. The method according to claim 1, said method comprising a step of reacting a compound represented by formula III:

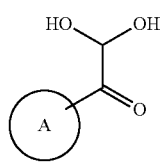

(III)

a salt thereof, or a derivative thereof with aminourea or a salt thereof in water to produce the compound represented by formula IV or a salt thereof, and then a step of subjecting the resulting compound or a salt thereof to the step(s) according to claim 1;
wherein the derivative of formula (III) is a compound represented by formula (III'):

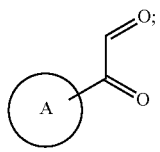

(III')

and
wherein ring A represents an optionally substituted aryl group or an optionally substituted heteroaryl group.

3. The method according to claim 2, said method comprising a step of subjecting the compound represented by formula IV or a salt thereof without isolation to the step(s) according to claim 1.

4. The method according to claim 3, said method comprising a step of collecting the compound represented by formula IV or a salt thereof by filtration.

5. The method according to claim 2, said method comprising a step of reacting a compound represented by formula II:

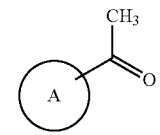

(II)

or a salt thereof with a glyoxalization reagent to produce the compound represented by formula III, a salt thereof, or the derivative thereof, and then a step of subjecting the resulting compound, a salt thereof, or the derivative thereof to the step(s) according to claim 2;
wherein ring A represents an optionally substituted aryl group or an optionally substituted heteroaryl group.

6. The method according to claim 5, said method comprising a step of subjecting the compound represented by formula III, a salt thereof, or the derivative thereof without isolation to the step(s) according to claim 2.

7. The method according to claim 1, wherein ring A is an optionally substituted monocyclic or bicyclic aryl group.

8. The method according to claim 7, wherein ring A is a monocyclic or bicyclic aryl group optionally substituted with 1 to 3 group(s) independently selected from the group consisting of a halogen atom, an alkyl group, and an alkoxy group.

9. A method for producing a compound represented by formula V:

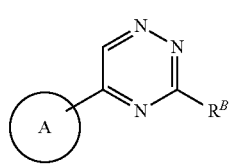

(V)

or a pharmaceutically acceptable salt thereof, said method comprising
a step of producing a compound represented by formula I:

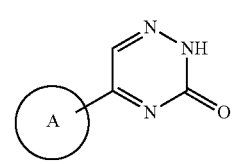

(I)

or a salt thereof by reacting a compound represented by formula IV:

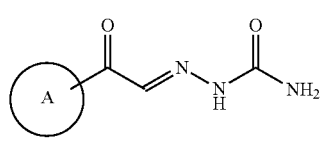

(IV)

or a salt thereof with a base in water, and optionally comprising a step of forming a salt thereof, and then
a step of producing the compound represented by formula V or a pharmaceutically acceptable salt thereof by a known method;
wherein ring A represents an optionally substituted aryl group or an optionally substituted heteroaryl group and $R^B$ represents an optionally substituted aliphatic heterocyclic group.

10. The method according to claim 9, wherein
ring A is an optionally substituted monocyclic or bicyclic aryl group; and
$R^B$ is a group represented by formula VI:

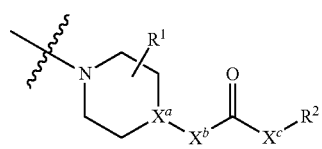

(VI)

wherein $X^a$ represents $CR^{3a}$ or N;
(i) when $X^a$ represents $CR^{3a}$, then
   $X^b$ represents $CHR^{3b}$ and $X^c$ represents O or $NR^{4c}$,
   $X^b$ represents O and $X^c$ represents $NR^{4c}$, or
   $X^b$ represents $NR^{4b}$ and $X^c$ represents O, $NR^{4c}$, or $CHR^{3c}$;
(ii) when $X^a$ represents N, then
   $X^b$ represents $CHR^{3b}$ or C(=O) and $X^c$ represents $NR^{4c}$, or
   $X^b$ represents $NR^{4b}$ and $X^c$ represents $CHR^{3c}$;
   $R^{3a}$ represents a hydrogen atom, a hydroxy group, an alkyl group, or an amino group;
   $R^{3b}$ and $R^{3c}$ represent each a group independently selected from the group consisting of a hydrogen atom, a hydroxy group, and an alkyl group;
   $R^{4b}$ and $R^{4c}$ represent each a group independently selected from the group consisting of a hydrogen atom, an alkyl group, and a cycloalkyl group;
   $R^1$ represents a hydrogen atom or an alkyl group;
   $R^2$ represents
(i) an optionally substituted alkyl group,
(ii) an optionally substituted cycloalkyl group,
(iii) an optionally substituted aliphatic heterocyclic group,
(iv) an optionally partially hydrogenated and optionally substituted heteroaryl group, or
(v) a hydrogen atom, or
   when $X^c$ represents $NR^{4c}$, then $R^2$ and $R^{4c}$ are combined with each other at their terminals together with the nitrogen atom to which they are attached to form an aliphatic heterocyclic group optionally substituted with an optionally substituted alkyl group; and
   the wavy line represents the point of attachment to the rest of molecule.

11. The method according to claim 10, wherein
   ring A is a monocyclic or bicyclic aryl group optionally substituted with 1 to 3 group(s) independently selected from the group consisting of a halogen atom, an alkyl group, and an alkoxy group;
   $R^B$ is a group represented by formula VI;
   $X^a$ represents N;
   $X^b$ represents $CHR^{3b}$ or C(=O);
   $X^c$ represents $NR^{4c}$;
   $R^{3b}$ represents a group independently selected from the group consisting of a hydrogen atom, a hydroxy group, and an alkyl group;
   $R^{4c}$ represents a group independently selected from the group consisting of a hydrogen atom, an alkyl group, and a cycloalkyl group;
   $R^1$ represents a hydrogen atom or an alkyl group;
   $R^2$ represents
(i) an optionally substituted alkyl group,
(ii) an optionally substituted cycloalkyl group,
(iii) an optionally substituted aliphatic heterocyclic group,
(iv) an optionally partially hydrogenated and optionally substituted heteroaryl group, or
(v) a hydrogen atom, or
   $R^2$ and $R^{4c}$ are combined with each other at their terminals together with the nitrogen atom to which they are attached to form an aliphatic heterocyclic group optionally substituted with an optionally substituted alkyl group.

12. The method according to claim 11, wherein
   ring A is a monocyclic or bicyclic aryl group optionally substituted with 1 to 3 group(s) independently selected from the group consisting of a halogen atom, an alkyl group, and an alkoxy group;
   $R^B$ is a group represented by formula VI;
   $X^a$ represents N;
   $X^b$ represents $CHR^{3b}$;
   $X^c$ represents $NR^{4c}$;
   $R^{3b}$ represents a group independently selected from the group consisting of a hydrogen atom, a hydroxy group, and an alkyl group;
   $R^{4c}$ represents a group independently selected from the group consisting of a hydrogen atom, an alkyl group, and a cycloalkyl group;
   $R^1$ represents a hydrogen atom or an alkyl group;
   $R^2$ represents
(i) an optionally substituted alkyl group,
(ii) an optionally substituted cycloalkyl group, or
(iii) an optionally substituted aliphatic heterocyclic group.

13. The method according to claim 12, wherein
   ring A is a monocyclic aryl group optionally substituted with 1 to 3 group(s) independently selected from the group consisting of a halogen atom, an alkyl group, and an alkoxy group;
   $R^B$ is a group represented by formula VI;
   $X^a$ represents N;
   $X^b$ represents $CH_2$;
   $X^c$ represents NH;
   $R^1$ represents a hydrogen atom;
   $R^2$ represents an optionally substituted cycloalkyl group.

14. The method according to claim 13, wherein
   ring A is a phenyl group optionally substituted with 1 to 3 group(s) independently selected from the group consisting of a halogen atom, an alkyl group, and an alkoxy group;
   $R^B$ is a group represented by formula VI;
   $X^a$ represents N;
   $X^b$ represents $CH_2$;
   $X^c$ represents NH;
   $R^1$ represents a hydrogen atom;
   $R^2$ represents an optionally substituted cyclohexyl group.

15. The method according to claim 14, wherein
   ring A is 4-methylphenyl;
   $R^B$ is a group represented by formula VI;
   $X^a$ represents N;
   $X^b$ represents $CH_2$;
   $X^c$ represents NH;
   $R^1$ represents a hydrogen atom;
   $R^2$ represents an optionally substituted cyclohexyl group.

* * * * *